United States Patent
Cohen et al.

(10) Patent No.: US 11,949,545 B2
(45) Date of Patent: Apr. 2, 2024

(54) COMPENSATION OF MOTION IN A MOVING ORGAN USING AN INTERNAL POSITION REFERENCE SENSOR

(71) Applicant: St. Jude Medical International Holding S.à r.l., Luxembourg (LU)

(72) Inventors: Amit Cohen, Binyamina (IL); Uzi Eichler, Haifa (IL); Alon Izmirli, Ganot Hadar (IL)

(73) Assignee: ST. JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 631 days.

(21) Appl. No.: 17/141,777

(22) Filed: Jan. 5, 2021

(65) Prior Publication Data
US 2021/0168013 A1 Jun. 3, 2021

Related U.S. Application Data

(60) Division of application No. 16/059,557, filed on Aug. 9, 2018, now Pat. No. 10,917,281, which is a
(Continued)

(51) Int. Cl.
*H04L 27/34* (2006.01)
*A61B 6/00* (2006.01)
(Continued)

(52) U.S. Cl.
CPC ............ *H04L 27/3405* (2013.01); *A61B 6/12* (2013.01); *A61B 6/5264* (2013.01); *A61B 6/527* (2013.01);
(Continued)

(58) Field of Classification Search
CPC ..... H04L 27/3405; A61B 6/12; A61B 6/5264; A61B 6/527; A61B 34/20; A61B 6/503;
(Continued)

(56) References Cited

U.S. PATENT DOCUMENTS 4,241,608 A * 12/1980 Dees .................... G01S 7/52074
73/626
5,577,502 A 11/1996 Darrow et al.
(Continued)

FOREIGN PATENT DOCUMENTS

EP 0916966 * 5/2002 ............... G01S 7/52
JP 3639857 * 2/2005 ............. A61B 6/025
(Continued)

OTHER PUBLICATIONS

"International Search Report and Written Opinion of the International Searching Authority", PCT/US2010/050224, dated Nov. 9, 2010.
(Continued)

*Primary Examiner* — Jerome Grant, II
(74) *Attorney, Agent, or Firm* — Billion & Armitage

(57) ABSTRACT

An apparatus for displaying a moving region of interest located within a body includes a positioning system to determine a position and orientation (P&O) of a medical device as well as to track, using an internal position reference sensor, the motion of the region of interest over time. A compensation function block generates a motion compensation function based on the motion of the region of interest, which is configured to compensate for the motion of the region of interest between a first time, for example a time at which an image was acquired and a second time, for example a time at which a P&O of the device was measured. The measured P&O is corrected using the compensation function. A representation of the medical device is superimposed on the image in accordance with the corrected P&O.

20 Claims, 4 Drawing Sheets

Related U.S. Application Data continuation of application No. 12/650,932, filed on Dec. 31, 2009, now Pat. No. 10,069,668.

(51) Int. Cl.
*A61B 6/12* (2006.01)
*A61B 34/20* (2016.01)
*G06T 7/33* (2017.01)
*A61B 6/50* (2024.01)
*A61B 17/00* (2006.01)
*A61B 90/00* (2016.01)

(52) U.S. Cl.
CPC ............... *A61B 34/20* (2016.02); *G06T 7/33* (2017.01); *A61B 6/503* (2013.01); *A61B 6/5235* (2013.01); *A61B 2017/00703* (2013.01); *A61B 2034/2051* (2016.02); *A61B 2090/376* (2016.02); *A61B 2090/3983* (2016.02); *G06T 2207/10121* (2013.01); *G06T 2207/30021* (2013.01); *G06T 2207/30048* (2013.01)

(58) Field of Classification Search
CPC ........ A61B 6/5235; A61B 2017/00703; A61B 2034/2051; A61B 2090/376; A61B 2090/3983; G06T 7/33; G06T 2207/10121; G06T 2207/30021; G06T 2207/30048
USPC .......................................... 382/128
See application file for complete search history.

(56) References Cited

U.S. PATENT DOCUMENTS

| | | | |
|---|---|---|---|
| 6,233,476 | B1 | 5/2001 | Strommer et al. |
| 7,197,354 | B2 | 3/2007 | Sobe |
| 7,343,195 | B2 | 3/2008 | Strommer et al. |
| 7,386,339 | B2 | 6/2008 | Strommer et al. |
| 11,026,660 | B2 * | 6/2021 | Sumi ...................... A61B 8/06 |
| 2001/0031919 | A1 | 10/2001 | Strommer et al. |
| 2005/0251028 | A1 | 11/2005 | Boese et al. |
| 2006/0058647 | A1 | 3/2006 | Strommer et al. |
| 2007/0049817 | A1 | 3/2007 | Preiss et al. |
| 2007/0106147 | A1 | 5/2007 | Altmann et al. |
| 2009/0149741 | A1 | 6/2009 | Heigl |
| 2009/0163800 | A1 | 6/2009 | Xu et al. |

FOREIGN PATENT DOCUMENTS

| | | | | |
|---|---|---|---|---|
| JP | 2007-500565 | A | | 1/2007 |
| JP | 2007-061617 | A | | 3/2007 |
| WO | 2000054689 | A1 | | 9/2000 |
| WO | 2004103182 | A1 | | 12/2004 |
| WO | WO2007095329 | | * 8/2008 | ............... G09G 3/22 |
| WO | 2009013661 | A2 | | 1/2009 |
| WO | 2009149409 | A1 | | 12/2009 |

OTHER PUBLICATIONS

Calvin R. Maurer, Jr., (Dec. 1996) "Registration of Multimodal Three-Dimensional Medical Images Using Points and Surfaces", [Doctoral Dissertation, Vanderbilt University].

* cited by examiner

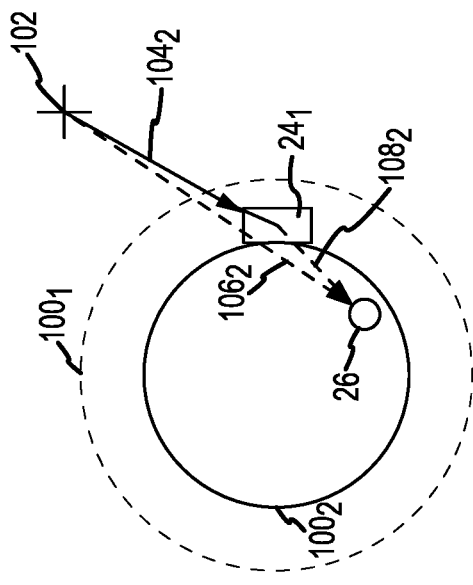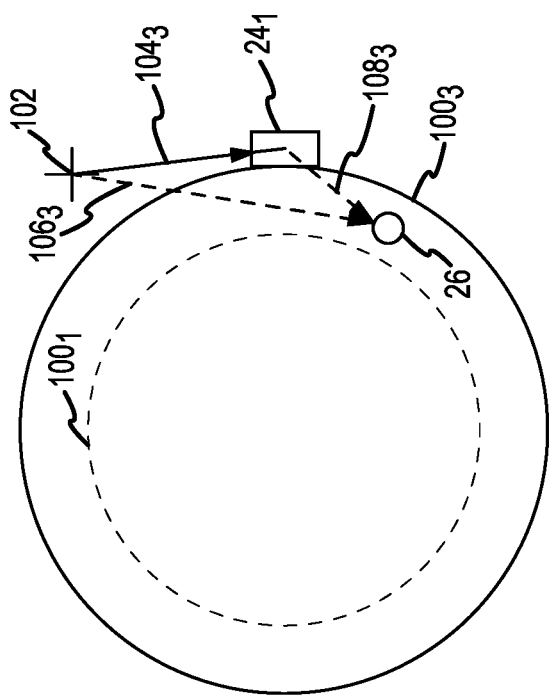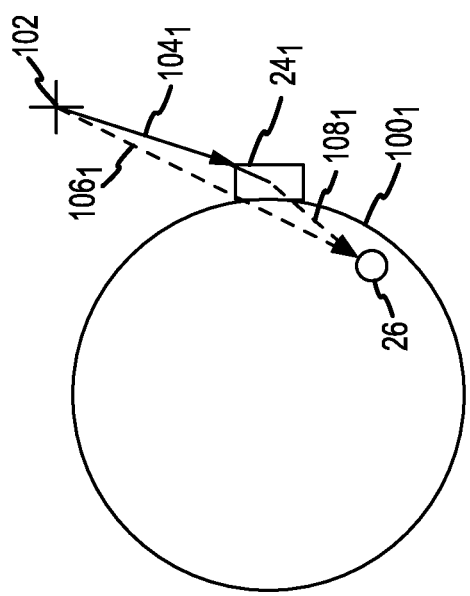

COMPENSATION OF MOTION IN A MOVING ORGAN USING AN INTERNAL POSITION REFERENCE SENSOR

CROSS-REFERENCE TO RELATED APPLICATIONS

This application is a divisional of U.S. application Ser. No. 16/059,557, filed 9 Aug. 2018 (the '557 application), now pending, which is a continuation of U.S. application Ser. No. 12/650,932, filed 31 Dec. 2009 (the '932 application), now U.S. Pat. No. 10,069,668. The '557 application and the '932 application are both hereby incorporated by reference as though fully set forth herein.

BACKGROUND OF THE INVENTION a. Field of the Invention

The instant invention relates generally to medical imaging and navigation and more particularly to a system and method for compensation of motion in a moving organ using an internal reference sensor.

b. Background Art

Systems and methods for obtaining and displaying two-dimensional and three-dimensional images are known in the art, for example, as seen by reference to U.S. Pat. No. 7,386,339 entitled "MEDICAL IMAGING AND NAVIGATION SYSTEM" to Strommer et al., hereby incorporated by reference in its entirety. Strommer et al. disclose a medical imaging and navigation system that has a capability for constructing and displaying three-dimensional images of moving organs, synchronously with the actual movement of these organs and synchronously with an invasive surgical tool, such as a catheter. The system includes a medical positioning system (MPS) for ascertaining the location and orientation of multiple MPS sensors, a two-dimensional imaging system having an image detector for obtaining two-dimensional images of the moving organ and a superimposing processor. The MPS system includes a sensor mounted on the surgical tool and a sensor attached to the body of the patient for a positional reference ("Patient Reference Sensor", or PRS). The system acquires a plurality of two-dimensional images (and respective location/orientation data and organ timing data, e.g., ECG signal) and records the sets of positions and orientation of all sensors. The system reconstructs a three-dimensional image from the combination of 2-D images and sensor data. When a physician inserts the surgical tool into the body of the patient, the system also detects the location and orientation of the MPS sensor that is mounted on the tool. The superimposing processor super-imposes a representation of the surgical tool on the currently displayed two-dimensional and three-dimensional images, which may be played back in accordance with real-time ECG data.

The PRS is provided so that the sensors associated with the surgical tools remain in a co-registered coordinate system to the X-ray imager at all times. The system detects movements of the patient using the PRS (e.g., patient body movements and respiration induced movements). The movements (as sensed by the PRS) are used to shift the coordinate system relative to the coordinate system in which the two-dimensional images were acquired. Therefore, in Strommer et al., the projection of real-time location information on previously recorded 2-D or 3-D images is both ECG synchronized and respiration compensated. However, in some situations, there is little or no correlation between the external motion compensation signals being used (i.e., the ECG signal and the PRS readings) and the internal motion of a region of interest. For example only, in the case of atrial fibrillation, the ECG signal may not effectively serve as a predictor or correlation input for the motion of the atria.

There is therefore a need for a system and method for compensation for the motion of a moving organ that minimizes or eliminates one or more of the problems set forth above.

BRIEF SUMMARY OF THE INVENTION

One advantage of the methods and apparatus described, depicted and claimed herein relates to the ability to accurately compensate for the motion of a moving region of interest in a patient's body (e.g., a moving organ such as the heart), such as may be needed when superimposing a representation of a catheter tip on an image acquired at a time different than a time when the position of the catheter tip was acquired.

This disclosure is directed to a method and apparatus for displaying a moving region of interest (ROI) located within a body. One embodiment of the method involves tracking the motion of the ROI over time and generating a motion compensation function. Next, determining a position and orientation (P&O) of an invasive medical device, such as, for example, a catheter. The next step involves correcting the determined P&O using the motion compensation function to thereby compensate for the motion of the ROI between a first time at which an image of the ROI was acquired and a second time (different than the first time) at which the P&O was determined. The next step involves superimposing a representation of the medical device onto the image in accordance with the corrected P&O.

In a preferred embodiment, tracking the motion of the region of interest involves associating a first localization sensor with the moving region of interest such that the sensor moves with the region of interest. Through this step, the localization system (e.g., a medical position system (MPS) in one embodiment) can acquire a first series of P&O readings, which readings define not only the motion of the sensor but also the motion of the region of interest. The method further involves acquiring a second series of P&O readings from a second localization sensor associated with the medical device. When the correlation between the first and second series of P&O readings exceeds a threshold, the system is enabled to perform motion compensation since the same motion of the region of interest can be assumed to influence the motion of the medical device. In one embodiment, the motion compensation function may comprise a time-varying vector displacement. Thus, for a given spatial position, for a given time, the function defines a vector displacement (and potentially rotation) by which the P&O of the medical device will need to be corrected so as to match its corresponding value at a time when the image was taken.

In still further embodiments, a plurality of localization sensors are deployed, where the compensation function is a weighted summation of the individual displacement vectors respectively attributed to the movements detected by the plurality of localization sensors. A weighting factor associated with each input may correspond to the correlation level observed for that input relative to the motion of the medical device.

These and other benefits, features, and capabilities are provided according to the structures, systems, and methods depicted, described and claimed herein.

BRIEF DESCRIPTION OF THE DRAWINGS

FIGS. 3A-3C are plan views showing the motion of a moving organ and the corresponding motion of an internal position reference sensor.

DETAILED DESCRIPTION OF THE INVENTION

Figure 1:
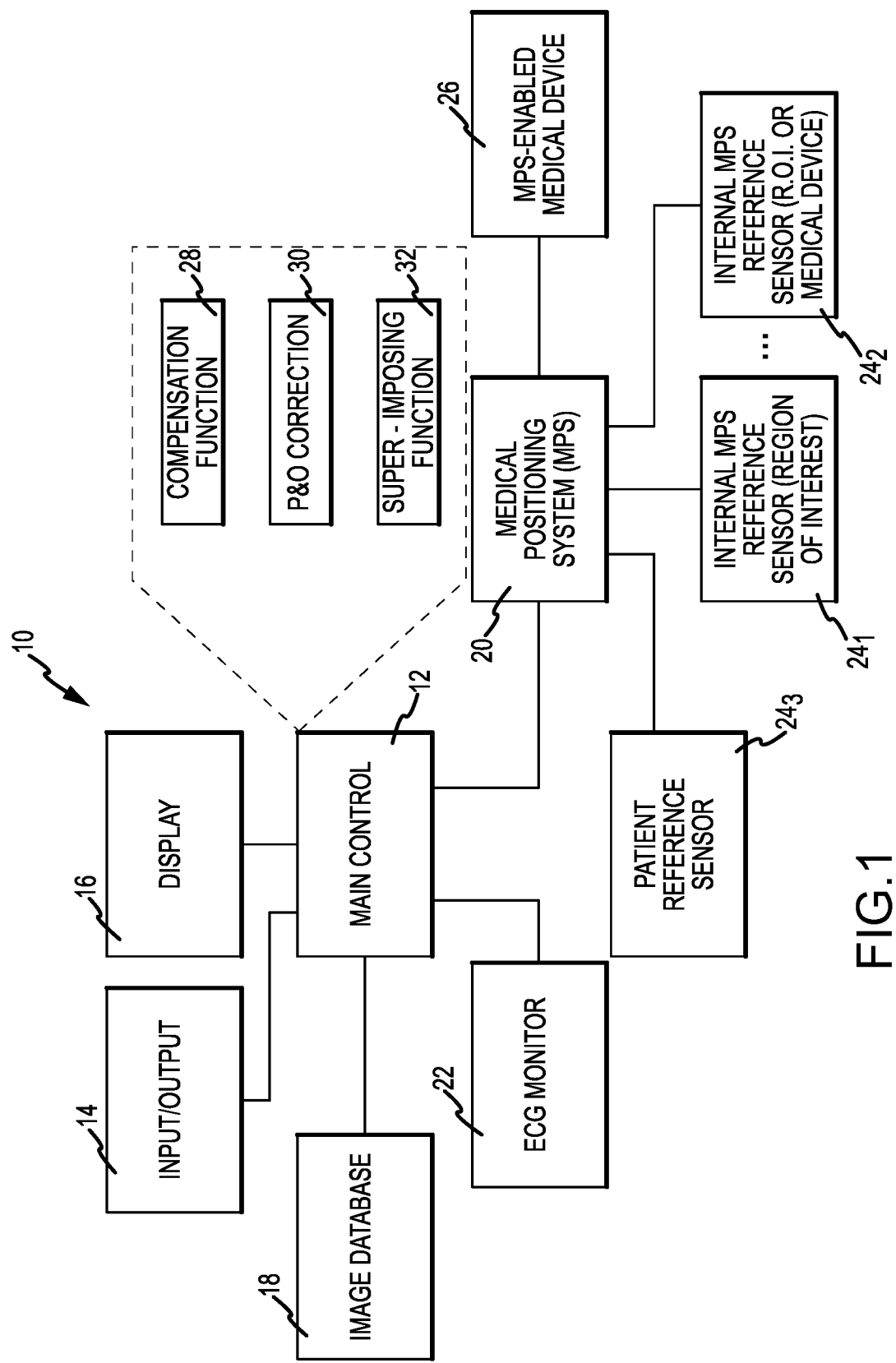
FIG. 1 is a schematic and block diagram view of a system incorporating an embodiment for compensation of motion in a moving organ using an internal position reference sensor.

Referring now to the drawings wherein like reference numerals are used to identify identical components in the various views, FIG. 1 is a diagrammatic view of a system 10 in which aspects of the invention may be embodied. It should be understood that while embodiments of the invention will be described in connection with a magnetic field-based positioning system deployed in connection with a fluoroscopy-based imaging system, such an embodiment is exemplary only and not limiting in nature.

Before proceeding to a detailed description keyed to the drawings, a general overview concerning motion compensation will be set forth. As a starting point, there is a desire to reduce a patient's exposure to x-rays, such as may be used in fluoroscopy. It is therefore desirable to be able to use, and reuse to the greatest extent possible, an image (or a sequence of images defining a cine loop) of a region of interest acquired in the past. This will reduce the need for continuous exposure or subsequent additional exposures for the purpose of acquiring updated imaging. Navigation of a medical instrument using the previously-acquired image or cine-loop is made possible by ascertaining the position and orientation (P&O) of the instrument and then superimposing a projection of that instrument's P&O onto the image. A problem arises over time, however, because both the patient as well as his or her internal organs can move (e.g., beating heart), changing positions relative to the time at which the image was taken. Absent compensation for these varying types of motion, the P&O readings reflecting the real time position of the medical instrument would be inaccurately represented on the image (i.e., the representation could be superimposed in the "wrong" location on the image). U.S. Pat. No. 7,386,339 referred to in the Background discloses motion compensation for patient movements and respiration-induced movements by providing a patient reference sensor (PRS). By interpreting P&O readings that track the motion of a catheter relative to the P&O readings of the PRS, a certain type of motion compensation can be achieved. In other words, the movements detected by the PRS shift the coordinate system relative to the coordinate system in which the two dimensional images were acquired. However, as also described in the Background, the PRS P&O readings may have little or no correlation to the movements of an internal moving organ.

With continued reference to FIG. 1, the system 10 as depicted includes a main control 12 having various input/output mechanisms 14, a main display 16, an image database 18, a localization system such as a medical positioning system (MPS) system 20, an ECG monitor 22, a plurality of MPS position reference sensors designated $24_1$, $24_2$ and $24_3$, and an MPS-enabled medical device 26 (which itself includes a position reference sensor). The MPS-enabled device 26 may be any interventional device or delivery tool. For example, the device 26 may include guidewires, stylets, cannulation catheters, EP catheters and the like.

The main control 12, in a computer-implemented embodiment, is programmed to perform a plurality of functions, including those shown in block form in FIG. 1: a motion compensation function 28, a position and orientation (P&O) correction function 30 and an image super-imposing function 32. The main control 12 is configured generally to generate data to be displayed (e.g., single image or sequence of images) corresponding to a moving region of interest (ROI) located within the body of a patient. The control 12 is specifically configured (by way of function blocks 28, 30 and 32) to accurately superimpose a representation of a tracked, MPS-enabled medical device 26 on a previously acquired image (or sequence) for display on the display 16, compensated for the motion of a moving region of interest. The input/output mechanisms 14 may comprise conventional apparatus for interfacing with a computer-based control, for example, a keyboard, a mouse, a tablet or the like. The display 16 may also comprise conventional apparatus.

The image database 18 is configured to store image information of relating to the patient's body, including the moving region of interest, and which may comprise (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from the ECG monitor 22. It should be understood that the two-dimensional images may be acquired through any imaging modality, now known or hereafter developed, for example X-ray, ultra-sound, computerized tomography, nuclear magnetic resonance or the like.

The MPS system 20 is configured to acquire positioning (localization) data (i.e., position and orientation—P&O) of one or more MPS sensors. The P&O may be expressed as a position (i.e., a coordinate in three axes X, Y and Z) and orientation (i.e., an azimuth and elevation) of the magnetic field sensor in the magnetic field relative to a magnetic field generator(s)/transmitter(s).

The internal MPS position reference sensor $24_1$ is associated with a moving region of interest (ROI) in the body, which may be a moving organ, and more specifically may be the heart and/or chambers or portions thereof (e.g., atria). The internal position reference sensor $24_1$ is associated with the ROI in such a way that it will move together with the moving ROI, and thus fairly indicate the motion of the region of interest. Generally, associating the sensor $24_1$ with the region of interest (ROI) may be done in any one or more ways: (1) placing the sensor $24_1$, or an interventional device like a catheter carrying the sensor $24_1$, in an anatomical area where it is held by the anatomy itself, for example, a catheter that has been maneuvered in a tubular organ like the coronary sinus; (2) fixing the sensor $24_1$, or an interventional device like a catheter carrying the sensor, to the anatomy in the region of interest using a fixation mechanism, active or passive, for the duration of the procedure; (3) holding the sensor $24_1$, or an interventional device like a catheter carrying the sensor, in steady contact with the anatomy in the region of interest; and (4) placing sensor $24_1$ (or interventional device carrying the sensor) in a non-MPS-enabled device that is in turn affixed to the anatomy in the region of interest. As to approach (2), where the region of interest is the heart, an example may include placing the sensor $24_1$ epicardially in the surface of the heart. As to approach (3), an example may include associating the sensor $24_1$ with a catheter that is maneuvered into steady contact with the heart interior. As to approach (4), an example may include placing an MPS-enabled guidewire (having the sensor $24_1$) in the lumen of a pacing lead that is in turn affixed to the tissue of a heart chamber.

One or more additional, optional internal position sensors may be provided, for example, as shown by sensor $24_2$. The additional one or more sensors $24_2$ may be associated with either or both of the (1) the moving region of interest; or (2) the medical device 26. The additional sensors $24_2$, are configured to provide additional data points (P&O readings) with respect to either the moving region of interest or medical device, as the case may be, thereby providing addition information concerning their respective motions over time.

The patient reference sensor (PRS) $24_3$ is configured to provide a stable, positional reference of the patient's body so as to allow motion compensation for gross patient body movements and/or respiration-induced movements, as described above. The PRS $24_3$ may be attached to the patient's manubrium sternum, a stable place on the chest, or other location that is relatively positionally stable.

In a magnetic field-based embodiment, the P&O may be based on capturing and processing the signals received from the magnetic field sensor while in the presence of a controlled low-strength AC magnetic field. Accordingly, the internal sensors may each comprise one or more magnetic field detection coil(s), and it should be understood that variations as to the number of coils, their geometries, spatial relationships, the existence or absence of cores and the like are possible. From an electromagnetic perspective—all sensors are created equal: voltage is induced on a coil residing in a changing magnetic field, as contemplated here. The sensors 24 are thus configured to detect one or more characteristics of the magnetic field(s) in which they are disposed and generate an indicative signal, which is further processed to obtain the P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. The ECG signal may be used by the main control 12 for ECG synchronized play-back of a previously captured sequences of images (cine loop). The ECG monitor 22 and ECG-electrodes may comprise conventional components.

Figure 2:
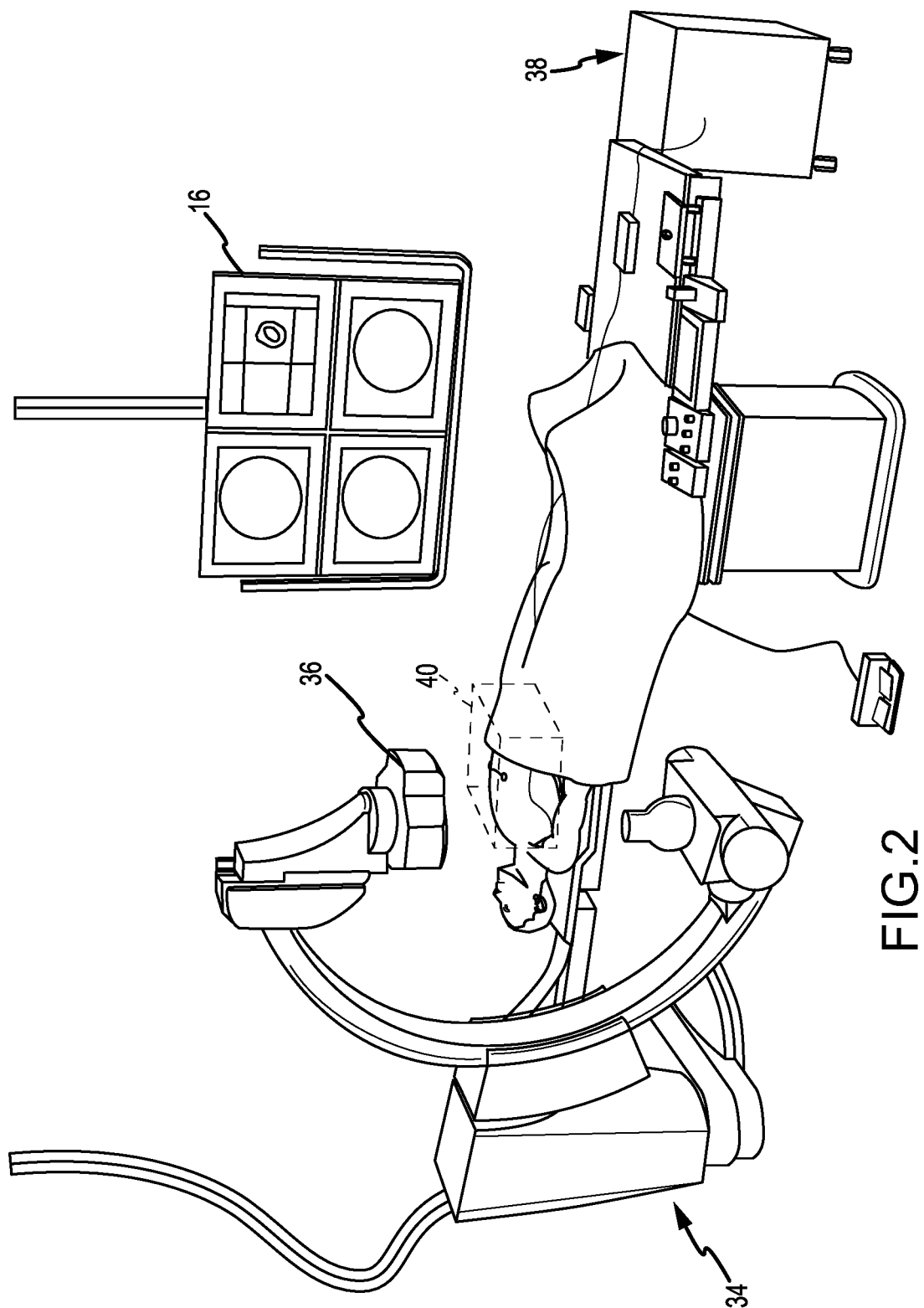
FIG. 2 is a diagrammatic view of the system of FIG. 1, in a fluoroscopy-based imaging embodiment.

FIG. 2 is a diagrammatic view of an embodiment which includes a self-contained imaging capability, along with motion compensation. More specifically, the system 10 is shown as being incorporated into an fluoroscopic imaging system 34, which may include commercially available fluoroscopic imaging components (i.e., "Catheter Lab"). The MPS system 20, in a magnetic field-based embodiment, includes a magnetic transmitter assembly (MTA) 36 and a magnetic processing core 38 for determining position and orientation (P&O) readings. The MTA 36 is configured to generate the magnetic field(s) in and around the patient's chest cavity, in a predefined three-dimensional space designated a motion box 40 in FIG. 2. The MPS sensors $24_i$ (where i=1, 2, . . . , n) as described above are configured to sense one or more characteristics of the magnetic field(s) and when the sensors are in the motion box 40, each generate a respective signal that is provided to the magnetic processing core 38. The processing core 38 is responsive to these detected signals and is configured to calculate respective three-dimensional position and orientation (P&O) readings for each MPS sensor $24_i$ in the motion box 40. Thus, the MPS system 20 enables real-time tracking of each sensor $24_i$ in three-dimensional space. In the illustrated embodiment, the positional relationship between the image coordinate system and the MPS coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is imported from an external source, a registration step may need to be performed initially. One exemplary embodiment of an MPS system 20 will be described in greater detail below in connection with FIG. 4.

The main control 12, as configured by way of superimposing function block 32, includes the capability of producing (and superimposing) a projection of the real-time location information (P&O) of a medical device on previously recorded x-ray images or in the case of cine-loops (CL), onto each image in the sequence. In addition, with the availability of the ECG signal and a PRS position signal, the main control 12 can replay a cine loop in an ECG synchronized and respiration-induced motion compensated manner. In a specific case of ECG synchronizing playback of a cine loop of the heart, the sequence is replayed in concordance with a real-time ECG signal (cardiac phase) of the patient. The main control 12 may also be configured to include a respiration compensation algorithm configured to learn the motion induced by the patient's respiration, based on P&O readings from the PRS. The main control 12 then calculates a respiration correction factor to apply to P&O measurements that are to be projected onto a sequence of cine-loop images. The PRS position signal allows for motion compensation for any patient's body movements, as the medical device's position (i.e., P&O measurement) may preferably be taken relative to the P&O measurements from the PRS.

However, as noted above, there are situations where there is very little or no correlation between the internal motion of the region of interest and the external signals (i.e., ECG signals and PRS signal) conventionally used for motion compensation. For example, in the case of atrial fibrillation, the ECG signal cannot serve as a predictor or correlation input for the motion of the atria.

Accordingly, one or more of the internal (i.e., inside the body) position reference sensors (e.g., sensor 24i) are located in the vicinity of the region of interest, or are otherwise associated with the region of interest (e.g., affixed) such that the internal MPS reference sensor moves together with the region of interest over time. As the region of interest moves, the MPS system 20 acquire a series of location (i.e., position and orientation) readings from the sensor. The motion compensation function block 28 (FIG. 1) determines the motion of the sensor (e.g., sensor $24_1$) according to acquired series of P&O readings. The block 28 further determines the motion of the region of interest based on the motion of the sensor, which may have a direct correspondence.

FIGS. 3A-3C are schematic diagram views of a region of interest, generally referenced 100, at three different activity states (states of movement), designated $100_1$, $100_2$ and $100_3$. In FIGS. 3A-3C, an internal MPS position reference sensor $24_1$ is placed in the vicinity of the region of interest 100 (e.g., at the orifice of the superior vena cava). In FIGS. 3A-3C, the region of interest 100 is depicted as a circle for simplicity.

In FIG. 3A, the region of interest $100_1$ is at a first activity state. The MPS system 20 detects a first position of the sensor $24_1$ at the first activity state. This first position (P&O) is represented as a vector $104_1$ relative to an arbitrary origin 102. The arbitrary origin 102 may be, for example, the location of the MTA 36 in the MPS system 102, a location on the motion box 40 or any other known location.

In FIG. 3B, the region of interest $100_2$ is at a second activity state, which as shown is contracted relative to the first activity state. The MPS system 20 detects a second position (i.e., position and orientation) $104_2$ of the sensor $24_1$. Note that the sensor $24_1$ moves with the region of interest as it moves.

In FIG. 3C, the region of interest $100_3$ is at a third activity state, which as shown is expanded relative to the first activity state. The MPS system 20 detects a third position (P&O) $104_3$ of the sensor $24_1$.

The series of detected first, second and third positions $104_1$, $104_2$ and $104_3$ of the sensor $24_1$ acquired by the MPS system 20 over time defines not only the motion of the sensor itself but also defines the motion of the region of interest. The motion compensation function block 28 may determine the motion of the region of interest 100 directly in accordance with the motion of the sensor $24_1$. This same motion can be assumed to influence the motion of the medical device 26, provided predefined criteria are met.

The criteria include verifying that an adequate level of correlation exists between the motion of the medical device 26 and the motion of the region of interest 100. One approach to verifying correlation is to compare the respective motions relative to a common time-line. For example, over some time interval, the system 10 may track the motion of the device 26, as indicated by the detected P&O's $106_1$, $106_2$ and $106_3$ shown in FIGS. 3A-3C, in addition to tracking the motion of the internal position sensor $24_1$. The system 10 compares the two motions and when the level of correlation exceeds a predetermined threshold, the correlation level is deemed adequate (predetermined criteria satisfied). In this regard, overall, the kind of correlation that is deemed adequate will vary; however, the ultimate goal is to reduce the amount of error (e.g., as expressed in millimeters). For this purpose (with the end goal in mind), correlation approaches may be determined empirically (e.g., bench testing). It should be further understood that the effect of the correlation threshold on the received error will also depend on the types of motions involved. Accordingly, motion compensation/correction will be performed.

The system 10 may additionally verify that a minimum level of correlation exists between the motion of the device 26 and the other compensation signals described above (i.e., the ECG signal(s) as well as the PRS signal). If there is only poor correlation between the motion of the device 26 and these compensation signals then compensation will not be performed at all. When motion correlation has been verified, the assumption that the motion of the region of interest will influence the motion of the device 26 can be relied on. After correlation has been verified, the MPS system 20 is then enabled to provide motion compensation.

Generate Motion Compensation Function. The MPS system 20 will generate data adequate to track the motion of a moving region of interest over time (e.g., via the internal sensor $24_1$) and allow the compensation function block 28 to generate a time varying motion compensation function. Just as the detected movements of the PRS allows shifting of the coordinate system (as described in U.S. Pat. No. 7,386,339), the motion of the internal sensor (e.g., sensor $24_1$) provides data adequate to implement a similar compensation function. For example in FIGS. 3A-3C, the position of the medical device 26 moves as the region of interest contracts (FIG. 3B) and expands (FIG. 3C). The relative displacement of the medical device 26 relative to the sensor $24_1$ (and thus also to the region of interest 100) is shown as vectors $108_1$, $108_2$ and $108_3$. Thus, one indication of the medical device's position is that taken relative to the sensor $24_1$.

The compensation function produced based on the motion of the sensor $24_1$ is a time-varying spatial function which accounts for the motion of the region of interest between a first time (at which the image was acquired) and a second time (at which the P&O of the device was measured). Assume that a two-dimensional image was acquired at a time when the region interest was in the first activity state $100_1$ (i.e., FIG. 3A). In this instance, a measured P&O of the device 26 would not need any motion compensation, at least not any to compensate for the motion of the region of interest. However, when the region of interest moves to the second activity state $100_2$, motion compensation is required to accurately project the measured P&O onto an image acquired at a time when the region of interest was at the first activity state (in this example). The compensation function evaluated at the time of the second activity state is a displacement vector that compensates for the motion of the region of interest between the given time (i.e., time of the measured device P&O—the time of the second activity state) and the time of the image (i.e., the time the image was acquired—the time of the first activity state). Likewise, the compensation function evaluated at the time of the third activity state $100_3$ is a displacement vector to compensate for motion between the given time (i.e., the time of the measured device P&O—the time of the third activity state) and the time of the image (i.e., the time the image was acquired—the time of the first activity state).

In sum, for a given spatial position (measured P&O) of the device 26 for a given time, the compensation function will constitute a vector displacement (and potentially rotation) by which the measured P&O of the MPS-enabled device 26 has to be corrected to match a given time in the past (i.e., at which the image was acquired). The displacement vector may be weighted in accordance with a weighting factor, which in turn may be calculated based on the calculated correlation level described above. Motion compensation approaches may be used as disclosed in U.S. Pat. No. 7,386,339 referred to above as well U.S. Pat. No. 7,343,195 (application Ser. No. 09/949,160 filed Sep. 7, 2001) entitled "METHOD AND APPARATUS FOR REAL TIME QUANTITATIVE THREE-DIMENSIONAL IMAGE RECONSTRUCTION OF A MOVING ORGAN AND INTRA-BODY NAVIGATION" to Strommer et al., the entire disclosures of both U.S. patents being hereby incorporated by reference herein.

P&O Correction. The P&O correction block 30 is configured to correct the P&O reading obtained at the given time using the compensation function. P&O correction function 30 adjusts the measured P&O of the medical device in accordance with the calculated displacement vector (and potentially rotation) described above.

Projection. Finally, a projection of the corrected P&O (three-dimensional) is made onto the two-dimensional image, with a representation of the medical device being superimposed on the image (e.g., may be cross-hairs representing the tip of a catheter or other representation). The resulting image may then be displayed on the display 16. One approach for projecting the corrected P&O onto a 2-D image is a direct consequence of the association of the MPS 3D coordinate system with the X-ray 2D coordinate system, as seen by reference to U.S. Pat. Pub. 2006/0058647, application Ser. No. 11/233,420 entitled METHOD AND SYSTEM FOR DELIVERING A MEDICAL DEVICE TO A SELECTED POSITION WITHIN A LUMEN, to Strommer et al., hereby incorporated by reference in its entirety. Once the coordinate systems are co-registered (a process that may be referred to a magnetic-optical calibration, which may be performed at the installation of the MPS system 20, as noted above), the coordinates of any 3D object (e.g., sensor, landmark or other artifacts) which needs to be displayed on a 2D image are multiplied by a coordinate transformation matrix that computes the corresponding 2D coordinates on the displayed image. This approach is exemplary only and not limiting in nature.

Multiple Inputs, Internal Sensors. In embodiments where the external PRS and/or additional internal position reference sensor inputs are used for motion compensation, the compensation function block 28 implements a composite motion compensation function that is formed by the summation of individual motion compensation contributions, i.e., the individual displacement vectors and (potentially rotations) attributable to each motion/sensor input (provided that correlation requirements are met, as described above). For example, additional sensors may be located on the medical device 26 or other medical devices and/or tools, for example, another MPS sensor disposed on a catheter, guidewire, etc. The P&O readings from additional internal sensors may reveal other movements or other aspects to the movements of the region of interest and/or the medical device.

The composite compensation function, for example, may include a number of terms where each term corresponds to an input, i.e., one term being provided with respect to the PRS, another term being provided with respect to the internal sensor $24_1$, still another term being provided with respect to an additional sensor $24_2$, and so on. In another embodiment, the inputs from the PRS, the ECG signals and the one or more internal MPS reference sensors may be used in combination to provide for robust motion compensation. In these embodiments, the individual inputs are weighted by a respective weighting factor to form a composite motion compensation function. The respective level of correlation is a principal factor according to which each weighting factor is determined. The weighted function can be depicted as weighted vector summation of the compensation function vectors.

Figure 4:
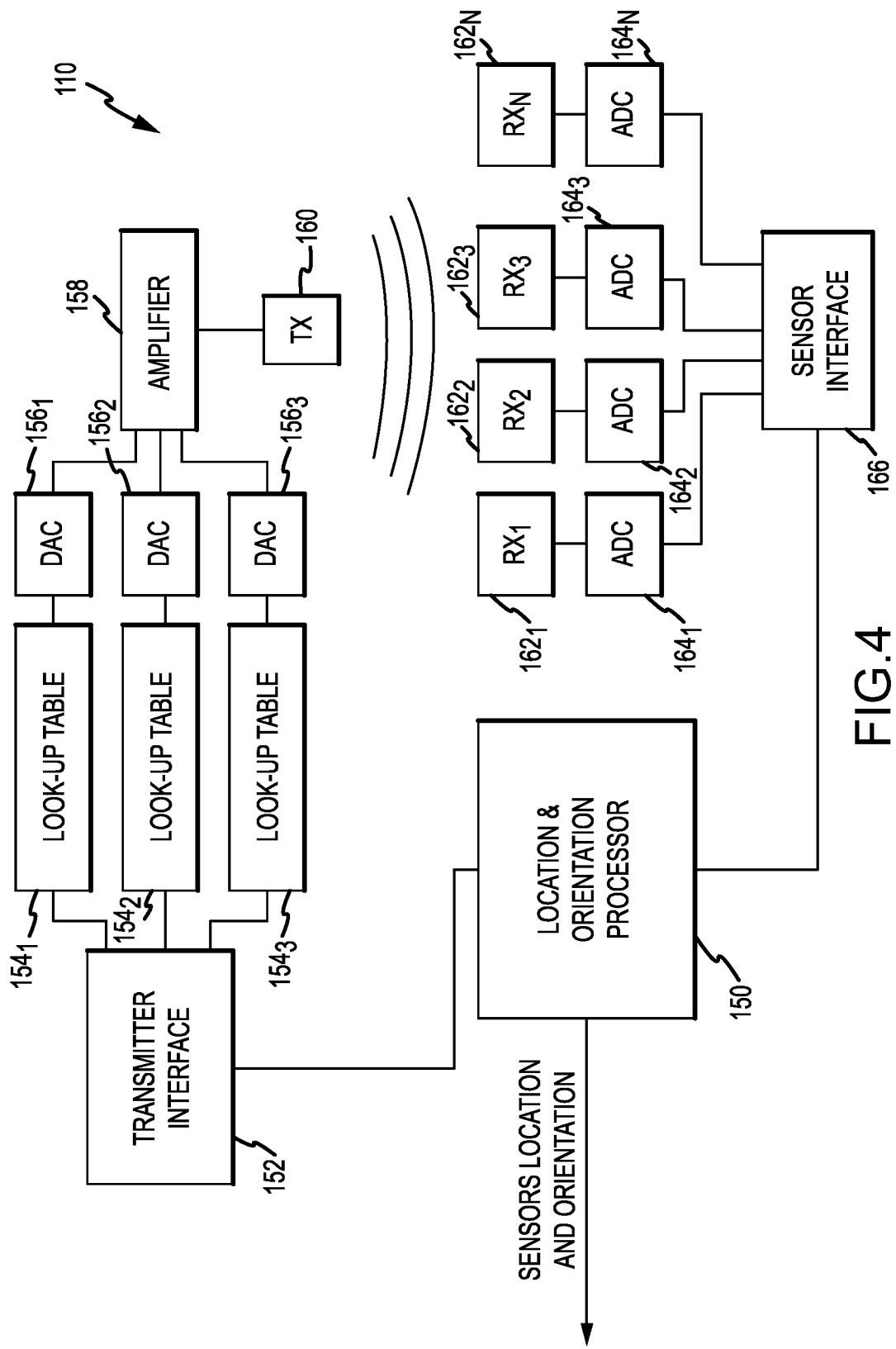
FIG. 4 is a schematic and block diagram view of one exemplary embodiment of a medical positioning system (MPS) as shown in block form in FIG. 1.

FIG. 4 is a schematic and block diagram of one exemplary embodiment of MPS system 20, designated as an MPS system 108, as also seen by reference to U.S. Pat. No. 7,386,339, referred to above, and portions of which are reproduced below. It should be understood that variations are possible, for example, as also seen by reference to U.S. Pat. No. 6,233,476 entitled MEDICAL POSITIONING SYSTEM, also hereby incorporated by reference in its entirety. This description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that variations and other uses other than for the described imaging embodiments are possible. High-fidelity device positioning as provided through the motion compensation embodiments described herein may be used for alternate purposes such as for placing accurate landmarks (i.e., to serve as navigation references of other devices), for co-registration with other modalities (e.g., Ensite NavX, computed tomography (CT)), as well as for determining when or distinguishing between a "real" motion (i.e., like the actual moving of a catheter by the physician) has occurred versus what seems to be motion but is actually an external event, such as patient motion.

It should be understood that the system 10, particularly main control 12, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for determining a current position of an invasive medical device within a patient's body, comprising:
    associating a first localization sensor with the medical device and acquiring a first series of position readings from the first localization sensor over a time interval representing a first movement of the first localization sensor over the time interval;
    associating a second localization sensor with the medical device and acquiring a second series of position readings from the second localization sensor over the time interval representing a second movement of the second localization sensor over the time interval;
    determining a respective weighting factor associated with the first and second movements corresponding to a respective correlation level of the first and second movements relative to a motion of the medical device;
    generating a function comprising a weighted summation, using the determined weighting factors, of individual displacement vectors respectively attributed to the first and second movements; and
    determining the current position of the medical device using a prior determined position of the medical device and the generated function.

2. The method of claim 1 wherein said generating the compensation_function comprises:
    weighting each individual displacement vector by a respective one of the determined weighting factors; and
    forming the weighted summation using the weighted displacement vectors.

3. The method of claim 2 wherein said forming the weighted summation further comprises summing the weighted displacement vectors to form a composite displacement vector.

4. The method of claim 1 further comprising:
    providing at least one of the first and second localization sensors as a magnetic field sensor configured for use with a magnetic field-based positioning system.

5. The method of claim 1 further comprising:
    providing a third localization sensor and acquiring a third series of position readings from the third localization sensor over the time interval representing a third movement of the third localization sensor over the time interval, wherein the third localization sensor is configured to be attached externally to the body.

6. The method of claim 5 wherein the respective weighting factors associated with the first and second movements define first and second weighting factors, said method further comprising:
    determining a third weighting factor associated with the third movement wherein the third weighting factor corresponds to the correlation level of the third movement relative to the motion of the medical device.

7. The method of claim 5 wherein said generating the function comprises:
    forming the weighted summation using the first, second, and third weighting factors and individual displacement vectors respectively attributed to the first, second, and third movements.

8. The method of claim 1 further comprising:
    acquiring an electro-cardiogram (ECG) signal indicative of the electrical activity of a heart organ and corresponding to a phase of a cardiac cycle of the heart organ.

9. The method of claim 8 wherein the respective weighting factors associated with the first and second movements define first and second weighting factors, said method further comprising:
    determining a third weighting factor associated with a third movement wherein the third movement is associated with the motion of the heart organ, and wherein the third weighting factor corresponds to the correlation level of the third movement relative to the motion of the medical device.

10. The method of claim 9 wherein said generating the function comprises:
    forming the weighted summation using the first, second, and third weighting factors and individual displacement vectors respectively attributed to the first, second, and third movements.

11. A system for determining a current position of an invasive medical device within a patient's body, comprising:
    a positioning system configured to acquire, from a first localization sensor associated with the medical device, a first series of position readings over a time interval representing a first movement of the first localization sensor over the time interval, the positioning system being further configured to acquire, from a second localization sensor associated with the medical device, a second series of position readings over the time interval representing a second movement of the second localization sensor over the time interval;
    a control unit including a first function block configured to determine a respective weighting factor associated with the first and second movements wherein the weighting factors correspond to a respective correlation level of the first and second movements relative to a motion of the medical device, the first function block being further configured to generate a function comprising a weighted summation, using the determined weighting factors, of individual displacement vectors respectively attributed to the first and second movements; and wherein the control unit further includes a second function block configured to determine the current position of the medical device using a prior determined position of the medical device and the generated function.

12. The system of claim 11 wherein the first function block is further configured to weight each individual displacement vector by a respective one of the determined weighting factors and form the weighted summation using the weighted displacement vectors.

13. The system of claim 12 wherein the first function block is further configured to sum the weighted displacement vectors to form a composite displacement vector.

14. The system of claim 11 wherein the positioning system is a magnetic field-based positioning system and wherein at least one of the first and second localization sensors comprises a magnetic field sensor.

15. The system of claim 11 wherein the positioning system is further configured to acquire a third series of position readings from a third localization sensor associated over the time interval representing a third movement of the third localization sensor over the time interval, wherein the third localization sensor is configured to be attached externally to the body.

16. The system of claim 15 wherein the respective weighting factors associated with the first and second movements define first and second weighting factors, the first function block being further configured to determine a third weighting factor associated with the third movement wherein the third weighting factor corresponds to a correlation level of the third movement relative to the motion of the medical device.

17. The system of claim 16 wherein the first function block is further configured to form the weighted summation using the first, second, and third weighting factors and individual displacement vectors attributed to the first, second, and third movements.

18. The system of claim 11 further comprising an electro-cardiogram monitor coupled to the control unit and configured to output an electro-cardiogram (ECG) signal indicative of electrical activity of a heart organ.

19. The system of claim 18 wherein the respective weighting factors associated with the first and second movements define first and second weighting factors, and wherein the first function block is configured to determine a third weighting factor associated with a third movement wherein the third movement is associated with the motion of the heart organ, and wherein the third weighting factor corresponds to the correlation level of the third movement relative to the motion of the medical device.

20. The system of claim 19 wherein the first function block is configured to form the weighted summation using the first, second, and third weighting factors and individual displacement vectors respectively attributed to the first, second, and third movements.

* * * * *